United States Patent [19]

Makino et al.

[11] Patent Number: 5,634,900

[45] Date of Patent: Jun. 3, 1997

[54] MULTI-DOSE POWDERED MEDICINE ADMINISTERING DEVICE AND METHOD THEREOF

[75] Inventors: Yuji Makino; Yoshiki Suzuki, both of Tokyo, Japan

[73] Assignee: Teijin Limited, Osaka, Japan

[21] Appl. No.: 373,202

[22] PCT Filed: May 12, 1994

[86] PCT No.: PCT/JP94/00771

§ 371 Date: Jan. 12, 1995

§ 102(e) Date: Jan. 12, 1995

[87] PCT Pub. No.: WO94/26338

PCT Pub. Date: Nov. 24, 1994

[30] Foreign Application Priority Data

May 12, 1993 [JP] Japan .................... 5-110412

[51] Int. Cl.$^6$ .................................................. A61M 13/00
[52] U.S. Cl. ................................ 604/58; 128/203.15
[58] Field of Search ......................... 604/58, 27, 57, 604/59, 60, 62, 63, 71, 73, 131, 140, 68; 128/203.15, 203.23; 222/636

[56] References Cited

U.S. PATENT DOCUMENTS

| | | | |
|---|---|---|---|
| 5,383,850 | 1/1995 | Schwab et al. | 604/58 |
| 5,394,868 | 3/1995 | Ambrosio et al. | 128/203.23 X |

FOREIGN PATENT DOCUMENTS

| | | | |
|---|---|---|---|
| 0518087 | 12/1992 | European Pat. Off. | |
| 9106333 | 5/1991 | WIPO | 604/58 |
| 9210229 | 6/1992 | WIPO | |
| 9318812 | 9/1993 | WIPO | 604/58 |

*Primary Examiner*—Robert A. Hafer
*Assistant Examiner*—N. Kent Gring
*Attorney, Agent, or Firm*—Sughrue, Mion, Zinn, Macpeak & Seas

[57] ABSTRACT

An administering device capable of quantitatively spraying a multi-dose of powdered medicine includes a device body (1), a storage chamber (3) detachably provided in the device body, the storage chamber (3) being capable of storing powdered medicine, the amount of which corresponds to a plurality of administering operations, an accommodation chamber (10) capable of accommodating powdered medicine, the amount of which corresponds to a single administering operation, and a medicine dispensing rotor (6) movably attached to the device body. The medicine dispensing rotor communicates the accommodation chamber with the storage chamber at a charging position (3a) and communicates the accommodation chamber with the outside of the device body at an administering position (5a) so that the powdered medicine in the accommodation chamber can be administered. A cap (20) is provided for moving the medicine dispensing rotor between the charging position and the administering position. A pump means (8) is provided for injecting air into the storage chamber through the accommodation chamber at the charging position so that the powdered medicine in the storage chamber can be stirred and a predetermined quantity of powdered medicine that has been stirred can be charged from the storage chamber to the accommodation chamber by the suction force of the pump means and/or gravity.

18 Claims, 4 Drawing Sheets

MULTI-DOSE POWDERED MEDICINE ADMINISTERING DEVICE AND METHOD THEREOF

TECHNICAL FIELD

The present invention relates to a constant quantity feed device, and a method thereof, for feeding powder, and more particularly relates to a multi-dose powdered medicine administering device. Still more particularly, the present invention relates to a multi-dose powdered medicine administering device and method thereof by which a unit-dose of powdered medicine, of a constant quantity, is continuously extracted from a quantity of stored powdered medicine and given to the patient a unit-dose of medicine (adminstration of multi-dose).

The device of the present invention is used as a multi-dose powdered medicine dispenser by which a unit-dose of powdered medicine of a constant quantity can be continuously divided from a multi-dose of powdered medicine and administered into the body cavity such as the nasal cavity by spraying.

Further, the device of the present invention is used as a multi-dose powdered medicine dispenser by which a unit-dose of powdered medicine of a constant quantity can be quantitatively extracted from a larger quantity of powdered medicine and administered into the body cavity such as the trachea, a bronchus or a lung by means of inhalation.

BACKGROUND ART

Powdered medicine is administered into a body cavity such as the nasal cavity or the oral cavity, and air ways such as the trachea, a bronchus or a lung by means of spraying or inhalation. For example, powdered medicine is administered into the nasal cavity or the air ways of a patient suffering from nasal allergy or asthma. Recently, attention has been given to a drug delivery system in which medicine is absorbed into the bloodstream through the mucous membrane of the nasal cavity or lung and it is attempted to administer powdered medicine via the mucous membrane.

When medicine is administered in the above manner, a powdered medicine administering device is used. Powdered medicine administering devices are classified into two types according to the storage system for the powdered medicine.

In the first type of powdered medicine administering device, a quantity of powdered medicine to be administered in a single operation is accommodated in an appropriate container. A unit-dose powdered medicine is accommodated in an appropriate capsule. Therefore, a unit-dose of powdered medicine is administered at each administering operation. In the second type of powdered medicine administering device, a quantity of powdered medicine to be administered in a plurality of operations is accommodated in an appropriate container. Each time an administering operation is carried out, an accurate unit-dose of powdered medicine is extracted from the container in which the powdered medicine is accommodated. In the present invention, a quantity of powdered medicine to be administered in a single operation is defined as a unit-dose, and a quantity of powdered medicine to be administered in a plurality of operations is defined as a multi-dose. However, in some cases, an administering operation in which powdered medicine, accommodated in the form of a unit-dose, is administered for each unit-dose is referred to as a unit-dose, and an administering operation in which powdered medicine accommodated in the form of a multi-dose is administered for each unit-dose is referred to as a multi-dose.

As an example of the unit-dose powdered medicine administering device by which powdered medicine is sprayed into the nasal cavity, a powdered medicine administering device has been proposed by the present inventors (disclosed in Japanese Patent Publication No. 63-6024). Concerning the unit-dose inhaler by which powdered medicine is inhaled into the air ways, a large number of devices have been proposed. For example, there is provided an inhaler in which capsules made of nonpoisonous material such as gelatin are used. In each capsule, a predetermined quantity of unit-dose powdered medicine is accommodated. In this type of inhaler, a capsule opening device is provided, by which a hole is formed in a capsule inserted into the inhaler, that is, a capsule opening device is provided, by which a hole is formed by various means.

This accommodated powdered medicine is inhaled through a hole made in the capsule by the action of an air flow caused by the user. The empty capsule is taken out from the inhaler, and a new capsule is accommodated in the inhaler. In the inhaler of the prior art disclosed in the U.S. Pat. Nos. 3,906,950 and 4,013,075, when holes are made at both ends of a capsule, the capsule is held in a stationary condition while the powdered medicine is inhaled. The powdered medicine is taken out from the capsule by the action of an air flow passing through the capsule generated as a result of inhalation.

In the case of another type inhaler, as disclosed in the U.S. Pat. Nos. 3,807,400 and 3,991,761, a capsule is previously opened by an appropriate means, and then the capsule is moved by the action of an air flow generated by inhalation. Due to the foregoing action, the capsule is made completely empty.

In the case of still another type inhaler of the prior art disclosed in the European Patent Publication No. 0211595, a plurality of capsules are not used, but a disk-shaped pack is charged into the inhaler, and a series of bubbles are provided around the pack under the condition that the distances from the bubbles to center of the pack are the same. A predetermined quantity of powdered medicine is accommodated in these bubbles. This pack composes a portion of the inhaler and is put on a rotatable circular tray around the central axis. In this tray, holes are made at positions corresponding to each bubble, and when each bubble is moved and broken by an appropriate device, powdered medicine is taken out from the bubble and inhaled.

An example of the multi-dose powdered medicine administering device used for inhalation into the air ways is disclosed in the European Patent Publication No. 0069715. This multi-dose powdered medicine administering device includes a container accommodating a predetermined quantity of medicine, and a device for taking out powdered medicine accommodated in the container so as to prepare for the administration of the medicine. This administration preparation device is composed of a plate, the thickness of which is predetermined, and through-holes, the number of which is predetermined, are made in the plate. This plate is capable of moving from a position at which a portion of the through-holes are filled with powdered medicine taken out from the container by a mechanical means, to a position at which the holes filled with the medicine are located in the passage. When the user inhales through an inhalation port communicated with this passage, air enters the passage, so that powdered medicine can be taken out from the through-hole. There is provided a scraper, which scrapes powdered medicine on the container side in the through-hole made on the plate. According to the inventors who applied for the European Patent, the through-holes are completely filled with powdered medicine by the action of this scraper. Therefore, a constant dose can be ensured. According to this European Unexamined Patent Publication, it is described that the scraper is optionally provided. However, in order to appropriately operate the inhaler, it is necessary to provide the scraper. The reason is that the dose greatly differs when this scraper is not provided. The reason why is described as follows. Since the fluidity of the powdered medicine to be used is low, it frequently occurs that the individual through-holes are not completely filled with powdered medicine.

When a comparison is made between the unit-dose powdered medicine administering device and the multi-dose powdered medicine administering device, the multi-dose powdered medicine administering device tends to be preferably used from the viewpoint of convenience and marketability.

However, there is a serious problem to be solved in the conventional multi-dose powdered medicine administering device. As described above, according to the conventional multi-dose powdered medicine administering device, a quantity of powdered medicine necessary for one administering operation is continuously and quantitatively divided from a large quantity of collective powdered medicine and then the divided powdered medicine is administered. However, the above operation is very difficult in view of the physical property of powdered medicine such as a change in the density of collective powdered medicine and a tendency of collective powdered medicine.

In order to solve the above problems, several proposals have been made. For example, as disclosed in the aforementioned European Patent Publication No. 0069715 (Japanese Examined Patent Publication No. 1-47190), a through-hole, the capacity of which is predetermined, is continuously filled with powdered medicine pressed by a scraper. However, even when this method is adopted, the following problems may be encountered. For example, when the overall medicine administering device is vibrated, the bulk density of powdered medicine is changed, so that the actual quantity of powdered medicine filled into the through-hole is changed. As a result, the quantity of powdered medicine to be administered fluctuates.

In Japanese Unexamined Patent Publication No. 3-18376, a multi-dose medicine administering device is disclosed, in which a large quantity of powdered medicine is compressed, and the compressed body of powdered medicine is quantitatively divided into pieces. According to the above method, when powdered medicine is compressed, a quantity of divided medicine is ensured to be constant. However, even in this method, the following disadvantages may be encountered. By the influence of vibration given to the overall medicine administering device, the density of compressed powdered medicine is changed. As a result, the weight of the divided piece made of compressed powdered medicine is changed, so that a quantity of powdered medicine to be administered to a patient is changed.

SUMMARY OF THE INVENTION

It is an object of the present invention to provide a multi-dose powdered medicine administering device and method thereof by which a quantity of powdered medicine to be administered by a single operation, that is, a unit-dose of powdered medicine is continuously and quantitatively divided and administered even when some affects, such as vibration, is given to the overall medicine administering device from the outside.

Even if a unit-dose of medicine is continuously and quantitatively divided, when the operation of the device is complicated, patient's compliance is reduced. Therefore, it is an object of the present invention to provide a multi-dose powdered medicine administering device and method thereof in which a unit-dose of powdered medicine is continuously and quantitatively divided and administered in a simple operation.

In order to accomplish the above object, the present inventors made every effort and discovered that, for the purpose of continuously and quantitatively dividing a unit does of powdered medicine, it is necessary to prevent the density of a large quantity of collective powdered medicine stored in the storage chamber from changing. From the above viewpoint, the following conditions must be satisfied.

(1) Immediately before each dividing operation, air is pumped through the powdered medicine collectively stored in the storage chamber, so that the collective powdered medicine flows in the storage chamber.

(2) After that, a unit-dose of powdered medicine is accommodated in the powdered medicine accommodating chamber by the action of a suction force and/or gravity. When the above two conditions are satisfied, a unit-dose of medicine can be continuously and quantitatively divided into the accommodation chamber. In this connection, when air is pumped through the storage chamber in the process of item (1), it is very important to the fluidity of the powdered medicine in the storage chamber that the air flow is discharged outside the chamber through a filter attached to the chamber.

The present invention provides a multi-dose powdered medicine administering device comprising: a device body; a storage chamber detachably provided in the device body, the storage chamber being capable of storing a multi-dose of powdered medicine; an accommodation chamber capable of accommodating a unit-dose of powdered medicine; a medicine dispensing means movably attached to the device body, the medicine dispensing means communicating the accommodation chamber with the storage chamber at a charging position, the medicine dispensing means communicating the accommodation chamber with the outside of the device body at an administering position so that the powdered medicine in the accommodation chamber can be administered; a movement means for moving the medicine dispensing means between the charging and the administering positions; and a pump means for injecting air into the storage chamber through the accommodation means at the charging position so that the powdered medicine in the storage chamber can be stirred, wherein a predetermined quantity of powdered medicine that has been stirred is charged from the storage chamber to the accommodation chamber by the suction force of the pump means and/or gravity.

The above storage chamber is cylindrical, and one end of the storage chamber with respect to the axial direction is attached to a storage chamber mount portion of the device body having an opening for charging, and the other end of the storage chamber is closed by a filter through which air can be circulated but powdered medicine cannot be circulated.

The dispensing means is composed of a rotor rotatably attached to the device body. In the rotor, a plurality of through-holes are formed at regular intervals around the rotational axis of the rotor. A filter through which air can be circulated but that powdered medicine cannot pass is inserted and fixed to each through-hole. The accommodation chamber is defined by the filter. A pushing means for pushing the dispensing means to a portion of the device body is provided so that the opening of the accommodation chamber can be closed by the portion of the device body while the accommodation chamber moves at least from the charging position to the administering position.

The device body includes a flat plate portion. A charging opening and an administering opening are respectively formed at the charging and administering positions on the flat plate. A storage chamber mount portion for detachably mounting the storage chamber corresponding to the charging opening is provided on the one side of the flat plate portion.

The rotor is rotatably provided so that a surface of the accommodation chamber on the opening side can be contacted with the other surface of the flat plate portion. The accommodation chamber of the rotor is communicated with the storage chamber in the axial direction at the charging position through the storage chamber mount portion of the flat plate portion. The accommodation chamber of the rotor is aligned and communicated with the administering opening at the administering position in the axial direction.

At least two accommodation chambers are provided around the rotor axis at regular intervals. When the first accommodation chamber is located at the charging position, the second accommodation chamber is located at the administering position. When the rotor is rotated at intervals of 180°, each accommodation chamber is alternately located at the charging and administering positions, and the opening side of the accommodation chamber is contacted with and closed by the flat plate portion when the accommodation chamber is located between the charging and administering positions.

Alternatively, four accommodation chambers are provided around the rotor axis at intervals of 90°. The charging opening at the charging position and the administering opening at the administering position are symmetrically located with respect to the axis at intervals of 180° in the flat plate portion. The rotor is rotated at intervals of 90°, and the four accommodation chambers are successively located at the charging position, administration waiting position, administering position, and charge waiting position.

When this medicine administering device is constructed to be used as an inhaler, the device body includes a flat plate portion, a charge and an administration opening are formed at the charging and administering positions of the flat plate portion, a storage chamber mount portion is provided on one surface of the flat plate so that the storage chamber can be detachably mounted corresponding to the charge opening, and the pump means is composed of a returnable and flexible container or bladder attached to the device body, and the pump means supplies and sucks air only from the accommodation chamber located at the charging position through the filter wherein the supplying and sucking operation is conducted from the rotor side opposite to the flat plate portion.

When this medicine administering device is constructed to be used as a dispenser, the device body includes a flat plate portion, a charging opening and an administering opening are formed at the charging and administering positions of the flat plate portion, a storage chamber mount portion is provided on one surface of the flat plate so that the storage chamber can be detachably mounted corresponding to the charge opening, a nozzle mount portion to which a nozzle having an injection opening at its end is attached is also provided on one surface of the flat plate corresponding to the administration opening, and the pump means is composed of a returnable and flexible container or bladder attached to the device body, and the pump means supplies and sucks air from both accommodation chambers located at the charging and administering positions through the filter wherein the supplying and sucking operation is conducted from the rotor side opposite to the flat plate portion.

The device body my be composed in the following manner. The device body includes a disk portion and a cylinder portion formed integrally with the disk portion. The rotor is rotatably held inside of the cylinder portion so that one surface of the rotor in the axial direction can be maintained in a contact condition with the disk portion. A guide groove is formed in the axial direction on the cylinder portion. A helical groove is formed on the outer circumference of the rotor. A cam pin penetrating through the guide groove formed in the axial direction and engaging with the helical groove is provided on the inner surface of a cap capable of being attached to and detached from the cylinder portion. Each time the cap is attached to and detached from the cylinder portion, the rotor is rotated in a predetermined direction by a predetermined angle.

The rotor may be constructed in the following manner. The rotor is sandwiched between a flat plate and a draft means using a pin provided at the center and a spring engaging with the pin, so that the rotor is rotatably held by the pin. In this way, one of the surfaces of the rotor in the axial direction on which the accommodation chamber is open comes into contact with the flat plate portion, and the other surface on which the filter is provided comes into contact with the draft means.

Preferable examples of usable materials to compose the rotor having the powdered medicine storage chamber or the powdered medicine accommodation chamber of the present invention are: polymers such as polyethylene, polystyrene, polypropylene, styrene acrylonitrile polymer, and acrylonitrile-butadiene-styrene polymer; and polymers such as hydroxypropylmethyl cellulose, methyl cellulose, hydroxypropyl cellulose, starch, hydroxypropyl starch, sodium alginate, and polyvinyl alcohol or polymers containing at least two of these polymers. Dimensions of the powdered medicine storage chamber may be appropriately determined in accordance with the unit-dose or the volume and number of the powdered medicine accommodation chambers.

The device body (base body) of the present invention, the rotor closely contacted with the base body, the draft means closely contacted with the rotor, and the cap may be made of the same polymers as those composing the powdered medicine storage chamber.

The pump of the present invention is a factor for pressurizing air necessary for charging and/or spraying or sucking the powdered medicine. It is preferable that this pump is made of flexible material. Examples of usable flexible materials to make the pump are: resilient plastics such as polyethylene and polypropylene; and natural or synthetic rubber. Concerning the capacity of this pump, it is preferable that the pump has a capacity by which almost all powdered medicine accommodated in the powdered medicine accommodation chamber can be discharged when the pump is operated once or several times or ten times. When the apparatus is operated, air flows into the powdered medicine storage chamber only through a filter attached to the top of the powdered medicine storage chamber. However, it should be noted that the present invention is not limited to the specific filter, but any openings through which air flows may be adopted. Of course, it is possible that the powdered medicine storage chamber is formed into a closed system before it is used.

Examples of usable filters provided in the powdered medicine storage chamber or the powdered medicine accommodation chamber are: a mesh filter for sieve use and a membrane filter which are appropriately selected in accordance with the particle sizes of medicine and excipient (sometimes, medicine only). For example, in the case of spraying powdered medicine into the nasal cavity, a mesh filter, the sieve opening size of which is 5 to 37 μm and B preferably 5 to 10 μm, is used. Alternatively, a membrane filter, the opening size of which is 5 to 75 μm and preferably 5 to 25 μm, is used. In the case of spraying powdered medicine into the air path, a mesh filter, the sieve opening size of which is not more than 1 μm, is used. For example, a net for sieve use is made of nylon or stainless steel. For example, a membrane filter is made of polypropylene, cotton, rayon, glass fiber, or a sintered material.

A powdered medicine adaptable for the present invention can be composed of a medicine, and a conventional excipient such as lactose, starch, cellulose, and polyvinyl polymer. Alternatively a powdered medicine adaptable for the present invention can be composed only of medicine. When necessary, an additive such as a conventional stabilizer or an antioxidant may be appropriately added.

In the powdered medicine multi-dose administering device of the present invention, the powdered medicine storage chamber may be held separately from the powdered medicine accommodation chamber before the use, and they may be joined together when the device is put into use. Alternatively, the powdered medicine storage chamber, pump and powdered medicine accommodation chamber may be separate before use and be joined together when the device is put into use.

When the pump is operated, in the charging section, air is forced into the powdered medicine storage chamber by the air pressure generated by the pump. When air is discharged through the filter, the powdered medicine is pushed up and fluidized so that the powdered medicine is made to be uniform. Immediately after that, the powdered medicine is suddenly dropped due to the effect of both the suction force and gravity. In this case, the suction force is generated by a restoring force on the pump. Due to the foregoing, the powdered medicine is compressed and densely charged into the powdered medicine accommodation chamber.

When the pump is operated, in the administering section, pressurized air freely flows into the powdered medicine accommodation chamber in which the powdered medicine has already been accommodated, so that the powdered medicine passes through the nozzle together with pressurized air and is sprayed into the nasal cavity and others from an end of the nozzle.

Next, a cap is attached, and then a helicoid groove on the outer circumferential surface of the rotor is engaged with and moved along a cam pin provided on the inner circumferential surface of the cap. Therefore, the rotor is rotated by a predetermined angle again, and the powdered medicine accommodation chamber into which powdered medicine has been charged is moved to a waiting position for the administering section, and the powdered medicine accommodation chamber into which powdered medicine has not been charged yet is moved to a waiting position for the charging section. At this time, an upper surface of the powdered medicine accommodation chamber is rubbed by a lower surface of the base body, so that a predetermined amount of powdered medicine is accurately accommodated in the powdered medicine accommodation chamber.

When the rotor is manually rotated, the powdered medicine accommodation chamber is positioned in accordance with the click stop at the time when the rotation of the rotor is stopped, and further the powdered medicine accommodation chamber is positioned in accordance with the result of a visual check conducted when the base body is transparent.

As described above, by means of either an automatic or a manual rotation of the rotor, a multi-dose medicine administering device by which a unit-dose of powdered medicine is quantitatively administered can be provided.

MOST PREFERRED EMBODIMENT OF THE INVENTION

With reference to the example shown in the accompanying drawings, the multi-dose powdered medicine administering device of the present invention will be explained as follows.

Figure 1:
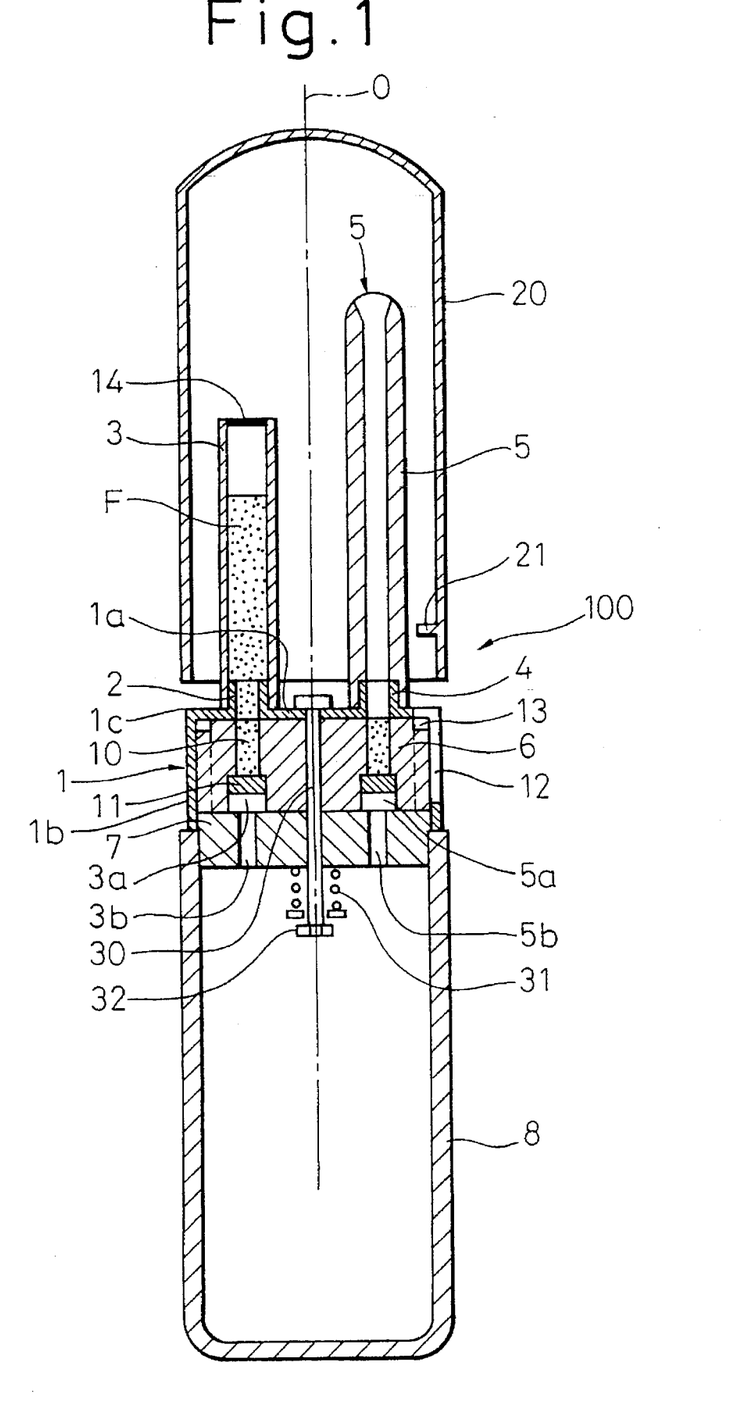
FIG. 1 is a sectional view of the overall arrangement of the multi-dose powdered medicine administering device for spraying use of Example 1 of the present invention.
Figure 2A:
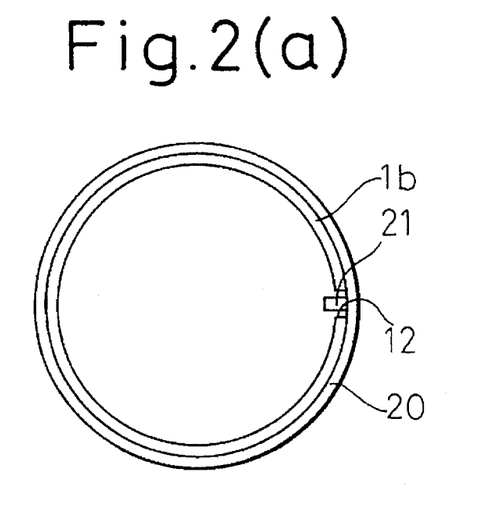
FIG. 2(a) is a sectional view of the cap of Example 1.
Figure 2B:
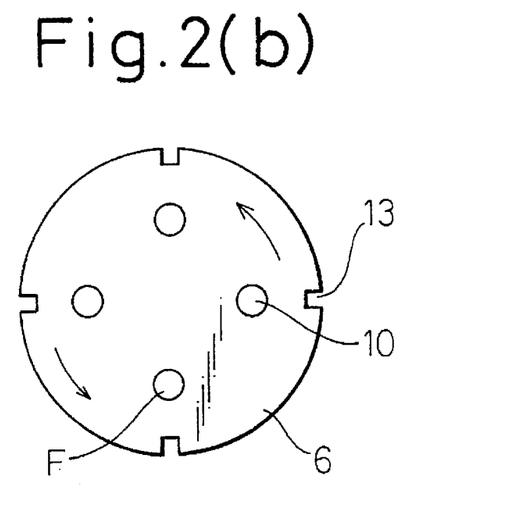
FIG. 2(b) is a sectional view of the rotor showing an arrangement of the powdered medicine accommodation chamber.
Figure 2C:
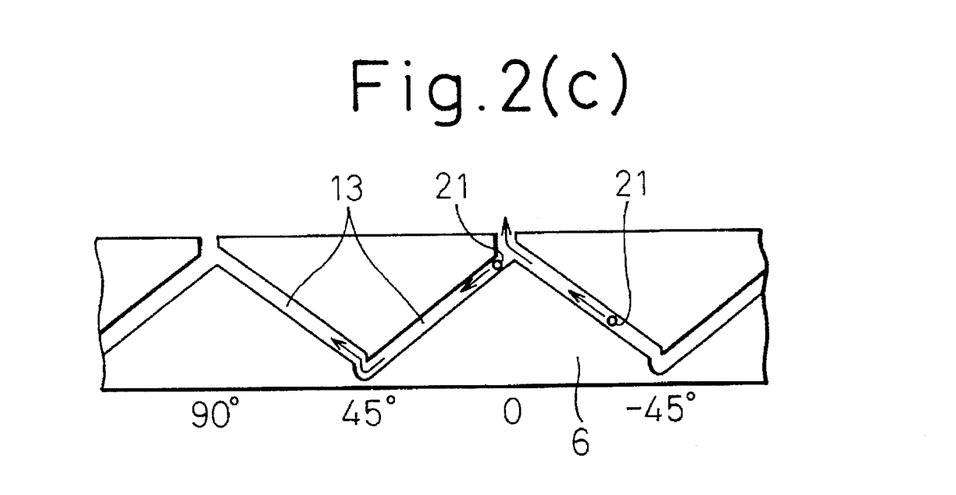
FIG. 2(c) is a development view of the helicoid groove provided on the side of the rotor.

FIG. 1 is a sectional view of the overall arrangement of the multi-dose powdered medicine administering device (100) of Example 1 of the present invention, FIG. 2(a) is a sectional view of the cap, FIG. 2(b) is a sectional view of the rotor, and FIG. 2(c) is a sectional view of the helicoid groove provided on the outer circumferential surface of the rotor.

In FIG. 1, numeral 1 is a base body of the apparatus. The base body 1 includes a circular roof plate 1a and a cup-shaped cylinder having a side plate (cylindrical portion) 1b which is formed integrally with the circular roof plate 1a. There are provided a powdered medicine storage chamber attaching section 2 and a nozzle attaching section 4 on an upper surface of the roof plate 1a. A cylindrical powdered medicine storage chamber 3 in which powder F is accommodated is detachably provided in the powdered medicine storage chamber attaching section 2, and a nozzle 5 is fixed to the nozzle attaching section 4. The base body 1 is made of transparent or translucent material, so that a powdered medicine accommodation chamber 10 provided in a rotor 6, which will be described later, can be checked by the visual inspection. At the top of the powdered medicine storage chamber 3, there is provided a filter 14 through which air passes.

It is preferable that the powdered medicine storage chamber attaching section 2 and the nozzle attaching section 4 are disposed on the circular roof plate 1a of the base body 1 in the following manner: With respect to the center line O, the powdered medicine storage chamber attaching section 2 and the nozzle attaching section 4 are disposed at the same distribution angle θ as that of the powdered medicine accommodation chamber 10 described later, or alternatively, the powdered medicine storage chamber attaching section 2 and the nozzle attaching section 4 are disposed at an angle given by integral multiples (for example, 60°, 90°, 180° and 120°), and they are disposed at positions equally distant from the center line O. In this example, the powdered medicine storage chamber attaching section 2 and the nozzle attaching section 4 are disposed at an angle of 180° around the center line O.

The powdered medicine storage chamber 3 is a stick-shaped, wide-mouthed or narrow-mouthed bottle, and charged with powdered or granular medicine F to be administered a plurality of times, that is, the quantity of the medicine is a multi-dose. The fore end of the nozzle 5 is rounded and there is provided a spraying opening 5c for spraying the medicine into the nasal cavity. In this connection, the storage chamber 3 may be screwed to the base body 1.

Numeral 6 is a rotor capable of rotating around the center line O, and an upper surface of the rotor 6 is closely contacted with a lower surface of the roof plate 1a of the base body 1. The rotor 6 may be made of transparent or translucent material so that the powdered medicine accommodation chamber 10 can be seen.

Numeral 7 is a draft means disposed close to the rotor 6. In the draft means 7, there are provided air passages 3b, 5b formed in the axial direction which are respectively located at a charging position 3a opposed to the powdered medicine storage chamber attaching section 2 in the axial direction and at an administering position 5a opposed to the nozzle attaching section 4 in the axial direction.

There is provided a through-hole which penetrates the roof plate 1a, rotor 6 and draft means 7 along the center line O. A pin 30 is inserted into this through-hole. A spring 31 is attached to an end of this pin 30 and fixed by a fixing means 32 of the prior art such as a washer and nut. Due to the foregoing construction, the rotor 6 is interposed between the roof plate 1a and the draft means 7 in a contact condition, further the rotor 6 is capable of rotating around the pin 30.

A plurality of powdered medicine accommodation chambers 10, in this example, 4 powdered medicine accommodation chambers 10 are provided in the rotor 6 being distributed at an appropriate distribution angle θ (at 90° in this example). At a position (the charging position 3a) on the lower side of the powdered medicine storage chamber attaching section 2, an upper surface of the powdered medicine accommodation chamber 10 is communicated with the powdered medicine storage chamber 3, and a lower surface of the powdered medicine accommodation chamber 10 is communicated with the air passage 3b. In the way described above, the powdered medicine accommodation chamber 10 is formed as a cylinder. In other words, when powdered medicine F in the powdered medicine storage chamber 3 is vibrated or sucked, it can be densely charged into the powdered medicine accommodation chamber 10. There is provided a filter 11 made of sintered ceramics etc. at a bottom of the powdered medicine accommodation chamber 10 (at a position close to the lower surface of the rotor 6). Accordingly, powdered medicine F is screened by the filter 11, and only an air flow passes through the filter. This filter 11 is press-fitted into the powdered medicine accommodation chamber 10 at a predetermined position. In this connection, the filter 11 may be provided in the draft means 7. In this case, it is preferable that the filter is disposed at an upper end of the draft means 7.

The powdered medicine accommodation chamber 10 is formed as a cylinder in such a manner that the upper surface is communicated with the nozzle 5 at a position on the lower side of the nozzle attaching section 4 (at the administering position) and the lower surface is communicated with the administering position 5a. Due to the foregoing construction, powdered medicine F can be injected into the nozzle 5 together with compressed air by the pressure of the air in the air passage 5b.

The powdered medicine accommodation chambers 10 are disposed at the same distribution angle so that they can be rotated by a predetermined angle in accordance with the rotation of the rotor 6. The powdered medicine accommodation chamber 10 is moved from the charging position 3a to the administering position 5a, and powdered medicine F charged at the charging position 3a is sprayed at the administering position 5a. After that, the powdered medicine accommodation chamber 10 is moved from the administering position 5a to the charging position 3a, and the empty powdered medicine accommodation chamber 10 from which powdered medicine F has been sprayed at the administering position is charged with powdered medicine F again at the charging position 3a.

For example, when the equal distribution angle θ of the accommodation chambers 10 is θ=180°, the operation is carried out as follows. When the rotor 6 is rotated by 180°, the powdered medicine accommodation chamber 10 charged with powdered medicine F at the charging position 3a is moved to the administering position 5a for spraying.

When the equal distribution angle θ of the accommodation chambers 10 is θ=90° like this example, the operation is carried out as follows. The powdered medicine accommodation chamber 10 charged with powdered medicine at the charging position 3a temporarily waits for the next operation at a position where it is rotated by 90°. At this time, the previous powdered medicine accommodation chamber 10 is subjected to injection at the administering position. When the powdered medicine accommodation chamber 10 is further rotated by 90°, it is moved to the administering position 5a, so that it is subjected to spraying. Since the upper and lower surfaces of the rotor 6 respectively come into contact with the roof plate 1a and the draft means 7, except for the powdered medicine accommodation chambers 10 located at the charging and administering positions 3a, 5a, the powdered medicine accommodation chambers 10 are closed, so that powdered medicine charged in the accommodation chambers 10 is not scattered.

Next, a rotational means for this rotor 6 will be explained as follows.

As described above, in the multi-dose powdered medicine administering device for spraying use of the present invention, when the rotor 6 is rotated by the equal distribution angle θ (by 90° in this example), the powdered medicine accommodation chamber 10 is moved in the mode of charging→waiting→injecting→waiting→→charging→ . . .

In this case, concerning the mechanism for rotating the rotor 6, various mechanisms may be adopted. As an automatic rotational means, it is possible to adopt a mechanism in which a cam groove is provided on the side of the rotor 6 as illustrated in FIGS. 1 and 2.

As illustrated in FIGS. 1 and 2, a helicoid groove 13 capable of rotating the rotor 6 by an angle of 45° is continuously formed on the side of the rotor 6 in the order of going, returning, going . . . , and a cam pin 21 capable of engaging with the helicoid groove 13 is provided on an inner surface of the cap 20. A straight guide groove 12 for guiding the cam pin 21 of the cap 20 in the axial direction is formed on a cylindrical side wall 1b of the base body 1. Accordingly, the cam pin 21 penetrates the guide groove 12 on the cylindrical side wall 1b and engages with the helicoid groove 13 of the rotor 6.

Consequently, when the cam pin 21 is engaged with both the guide groove 12 and helicoid groove 13, and pushes down the cap 20, the cam pin 21 is moved along the guide groove 12 in the axial direction, and the cap 20 is moved straight in the axial direction with respect to the base body 1. Since the cam pin 21 is moved along a going passage of the helicoid groove 13 of the rotor 6 at the same time, when the cam pin 21 arrives at the lowermost end, the rotor 6 is rotated by an angle of 45° that is half of the equal distribution angle θ. When the cap 20 attached to the base body 1 is pulled out, the cam pin 21 located at the lowermost end position is guided by the same guide groove 12 and moved straight, and at the same time, the cam pin 21 is moved along a returning passage of the helicoid groove 13, so that the rotor 6 is further rotated by an angle of 45°. As described above, when the cap 20 is attached to and detached from the base body, the rotor 6 is automatically rotated by an angle of 90° (=the equal distribution angle θ.

In this case, as illustrated in FIG. 2(c), a connecting section of the helicoid groove 13 for connecting the going passage with the returning passage is constructed in such a manner that the cam pin 21 comes into contact with the going passage at the upper end when the cam pin 21 is lowered, and on the other hand, the connecting section is constructed in such a manner that the cam pin 21 comes into contact with the returning passage at the lower end when the cam pin 21 is raised. Due to the foregoing construction, the rotor 6 is prevented from being reversed.

As a means for rotating the rotor 6 in the simplest manner, the rotor 6 may be manually rotated. To be more specific, an opening (not shown in the drawing) is formed at an appropriate position on the side of the base body 1, and a portion of the outer circumferential surface of the rotor 6 is exposed from the opening, and the operator rotates the rotor 6 with his finger. In this case, it is preferable that the rotor 6 is rotated only in one direction by the action of a one-way clutch (not shown in the drawing) and stopped with a click stop. Also, the rotor 6 may be made of transparent material so that a rotational position of the powdered medicine accommodation chamber 10 can be visually checked.

The pump 8 is composed of a bladder made of resilient material. An end of the pump 8 on the opening side is fixed to the peripheries of the cylindrical side wall 1b of the base body 1 and the draft means 7. In the case of pushing operation, air inside the pump is pressured so that air is sent to the charging position 3a and the administering position 5a, and in the case of releasing operation, air is sucked by the action of the resilience of the pump 8.

When the cap 20 is pulled out from the base body 1 in Example 1 described above, the cam pin 21 on the inner surface of the cap 20 moves straight by the action of the guide groove 12 and slides along the returning passage of the helicoid groove 13 being engaged with the groove, so that the rotor 6 is rotated by an angle of 45°. Due to the foregoing, the powdered medicine accommodation chamber 10 charged with powdered medicine, which has been waiting for the next operation at a position located at an angle of 45° before the administering position, moves to the administering position 5a. At the same time, the empty powdered medicine accommodation chamber 10, which has been waiting for the next operation at a position located at an angle of 45° before the charging position, is positioned at the charging position 3a.

When the pump 8 is activated, at the charging position 3a, air flows into the powdered medicine accommodation chamber 10 located at the charging position 3a through the air passage 3b of the draft means 7 and the filter 11, and then air flows out through the filter 14. At this time, powdered medicine F in the powdered medicine storage chamber 3 scatters upward and then drops and collides with the inside of the powdered medicine accommodation chamber 10. Therefore, powdered medicine F is compressed and densely charged into the powdered medicine storage chamber 3. When the rotor 6 closely coming into contact with the base body 1 is rotated, an upper surface of the powdered medicine accommodation chamber 10 is rubbed, so that a quantity of accommodated powdered medicine F can be accurately determined.

Also when the pump 8 is activated, compressed air flows into the powdered medicine accommodation chamber 10 through the air passage 5b and filter 11 at the administering position 5a. Then powdered medicine F in the powdered medicine accommodation chamber 10 is conveyed to the nozzle 5 together with the compressed air that has flown into the chamber. Further, powdered medicine F is sprayed, for example, into the nasal cavity from the spraying opening 5c provided at the end of the nozzle 5. Dimensions of the nozzle 5 are appropriately determined in accordance with the portion of the human body to be administered such as the nasal cavity and the oral cavity.

Next, the cap 20 is attached to the base body 1. Then the cam pin 21 engaging with the returning passage of the helicoid groove 13 of the rotor 6 moves, by the action of the guide groove 12, so that the rotor 6 is rotated by an angle of 45°. Then the powdered medicine accommodation chamber 10 charged with powdered medicine F at the charging position 3a stops at a position where upper and lower surfaces of the powdered medicine accommodation chamber 10 are not communicated with the outside air. When the cap 20 is pulled out, as described above, the powdered medicine accommodation chamber 10 charged with powdered medicine waiting for the next operation at a position before the administering position 5a is moved to the administering position 5a, so that the next spraying operation is ready to start.

It is possible that the series of charging and injecting operations described above is continued until powdered medicine F in the powdered medicine storage chamber 3 is used up. When a new powdered medicine storage chamber 3 is attached to the device, the operation can be continued.

Figure 3:
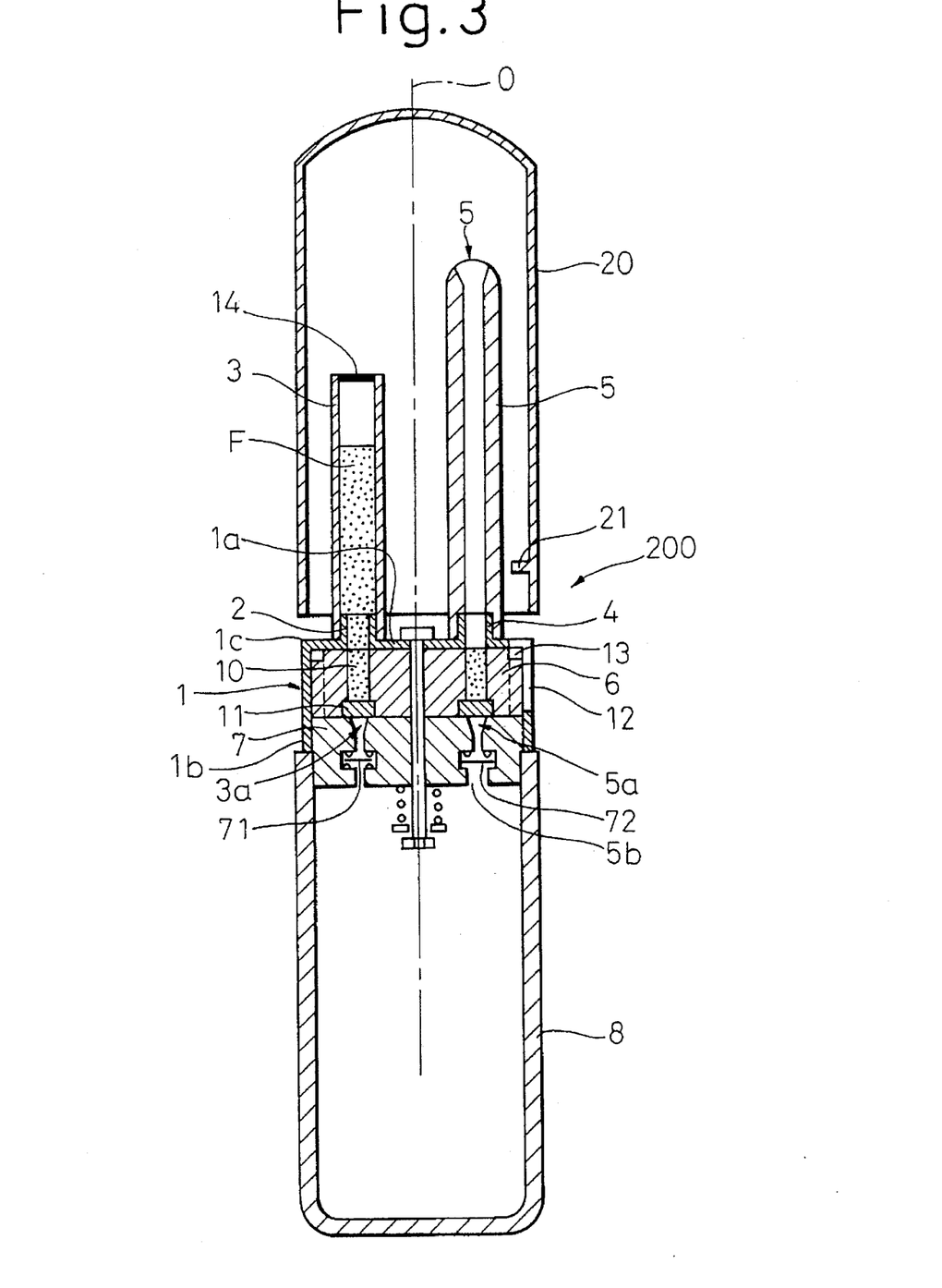
FIG. 3 is a sectional view of the overall arrangement of the multi-dose powdered medicine administering device for spraying use of Example 2.
Figure 4A:
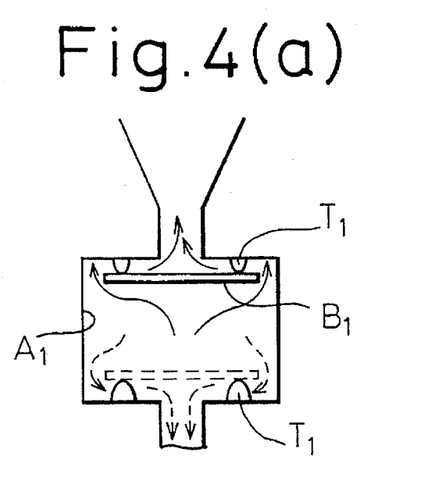
FIG. 4(a) is a schematic illustration showing the valve structure of the charging section in Example 2.
Figure 4B:
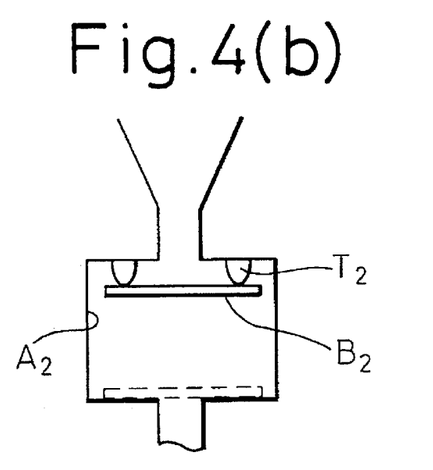
FIG. 4(b) is a schematic illustration showing the valve structure of the administering section in Example 2.

FIG. 3 is a sectional view showing the overall arrangement of the multi-dose powdered medicine administering device (200) of Example 2 of the present invention. FIG. 4(a) is a schematic illustration of the draft means at the charging position in Example 2. FIG. 4(b) is a schematic illustration of the draft means at the administering position.

Only the points different from Example 1 will be explained in the following. In this example, the thickness of the rotor 6 in the axial direction is slightly reduced, and the filter 11 is disposed at the bottom of the rotor 6. A two-way valve 71 capable of communicating in both the compression and suction processes is provided at the charging position 3a corresponding to the powdered medicine storage chamber attaching section 2 of the draft means 7, and a one-way valve 72 capable of communicating only in the compression process is provided at the administering position 5a corresponding to the nozzle attaching section 4.

In the two-way valve 71, a disk-shaped film B1, the diameter of which is a little smaller than that of a cylindrical air passage A1, is provided, and protrusions T1 are formed on the upper and lower surfaces of the air passage A1. Accordingly, even when the film B1 is located on either upper or lower surface of the air passage A1, a small clearance corresponding to the height of the protrusion T1 is provided between the air passage A1 and the film B1. Therefore, the air flow is not stopped although it is reduced.

Due to the foregoing construction, the operation is carried out as follows. When the pump 8 is activated so that it is contracted, compressed air freely flows from the pump 8 side into the powdered medicine storage chamber 3 by the action of the pump 8. After the film B1 has reached the upper surface, a small quantity of air flows into the powdered medicine storage chamber 3. In the same manner, when the pump 8 is activated so that it expands to the original configuration and sucks air, air freely flows out from the powdered medicine storage chamber 3 by the action of rise of the pump 8. After the film B1 has reached the lower surface, a small quantity of air flows out from the powdered medicine storage chamber 3. Due to the foregoing, simultaneously when the pump 8 starts the compressing operation, powdered medicine F in the powdered medicine storage chamber 3 is scattered upward and fluidized and, when the compressing operation is stopped and the sucking operation is started, powdered medicine F suddenly drops downward. Due to the foregoing, powdered medicine F is compressed and densely charged into the powdered medicine accommodation chamber 10.

On the other hand, at the administering position 5a of the draft means 7, there is provided a one-way valve 72 capable of communicating only in the process of compression. That is, the one-way valve 72 is constructed in the following manner. A disk-shaped film B2, the diameter of which is a little smaller than that of the cylindrical air passage A2, is inserted into the air passage A2, and a protrusion T2 is provided only on the upper surface of the air passage A2. In this case, it is constructed that the protrusion T2 is higher than the protrusion T1 of the two-way valve 71. Therefore, even when the film B2 is located on the upper surface, the air flow is only slightly reduced or throttled and it flows out upward. Powdered medicine F in the powdered medicine accommodation chamber 10 located at a position right above the administering portion 5a is sprayed, for example, into the nasal cavity from the spraying opening 5b formed at the end of the nozzle. In this connection, when the film B2 is located on the lower surface, the air passage A2 is completely stopped. Therefore, air does not flow backward from the spraying opening 5c of the nozzle 5 to the administering position 5a.

When the pump 8 is activated, at the charging position 3a having the valve 71, the disk-shaped film B1 in the air passage A1 is moved upward and contacted with the protrusion T1, so that a minute gap is formed. Then, a large amount of compressed air freely flows into the gap between the protrusion T1 and the film B1 only at the time of the rise. After that, a small amount of compressed air flows into the powdered medicine accommodation chamber 10 located at a position right above the charging portion 3a through the filter 11 and discharges outside through the filter 14. At this time, when compressed air freely flows into the chamber, the powdered medicine F in the powdered medicine storage chamber 3 scatters upward and drops downward so that the powdered medicine F collides with the inside of the powdered medicine accommodation chamber 10 and is compressed. In this way, the powdered medicine F is densely charged into the powdered medicine accommodation chamber 10. When the rotor 6 closely contacted with the base body 1 is rotated, the upper surface of the powdered medicine accommodation chamber 10 is rubbed, so that an amount of powdered medicine accommodated in the chamber can be correctly determined.

When the pump 8 is activated, in the administering portion 5a having the valve 72, the disk-shaped film B2 in the air passage A2 is moved upward and contacted with the protrusion T2. However, compressed air flows into the powdered medicine accommodation chamber 10 located right above the administering portion 5a through a gap formed between the protrusion T2 and the film B2 passing through the filter 11. Then the powdered medicine F in the powdered medicine accommodation chamber 10 is conveyed to the nozzle 5 together with the compressed air. Further the conveyed powdered medicine F is sprayed, for example, into the nasal cavity from the opening 5b provided at the end of the nozzle.

Other points of the construction and operation of Example 2 described above are the same as those of Example 1. Therefore, the explanations are omitted here.

In Examples 1 and 2, the multi-dose powdered medicine administering device of the present invention is explained. In the case of the multi-dose powdered medicine administering device for inhalation use, the method of dividing and accommodating a unit-dose of powdered medicine is the same as that of the multi-dose powdered medicine administering device for spraying use. Only one different point is a method of feeding the dividedly accommodated powdered medicine to a living body. That is, in the multi-dose powdered medicine administering device for spraying use, the powdered medicine is supplied to a living body by the administering device in such a manner that the powdered medicine is sprayed by the action of compressed air. In this case, the air pump for quantitatively dividing the unit-dose powdered medicine is used as the source of compressed air. However, in the case of inhalation, the most appropriate method is to transmit the medicine to the air ways of a patient using his respiration, and it is preferable that the medicine is not injected by a pump. Consequently, the administering portion may be open to the atmosphere through a one-way valve separate from the pump. The unit-dose powdered medicine in the powdered medicine accommodation chamber communicated with the nozzle is introduced into the air ways of a patient when an end of the nozzle is inhaled by the respiration of the patient.

[Industrially Applicable Field]

The multi-dose powdered medicine administering device of the present invention includes: a base body having a powdered medicine storage chamber and nozzle; a rotor closely contacted with the base body; a draft means closely contacted with the rotor; and a pump communicated with the draft means, wherein the rotor is provided with powdered medicine accommodation chambers capable of being positioned corresponding to a charging section for accommodating the unit-dose powdered medicine stored in the powdered medicine storage chamber and also capable of being positioned corresponding to an administering section for spraying from the nozzle. Accordingly, only when the rotor is rotated, the powdered medicine in the powdered medicine storage chamber can be quantitatively accommodated and set to an injecting section at the same time.

A helicoid groove capable of rotating at a predetermined angle is provided on the outer circumferential surface of the rotor, and a cam pin engaging with the helicoid groove is provided on the inner surface of a cap capable of being attached to and detached from the base body. Due to the foregoing construction, the powdered medicine accommodation chamber can be moved to a predetermined position when the cap is attached to and detached from the base body.

When the rotor is constructed in such a manner that the rotor can be manually rotated from the outside, the powdered medicine accommodation chamber can be positioned using a simple structure.

As a result of the foregoing, it is possible to provide a powder spraying and inhaling device capable of accurately spraying and inhaling a predetermined amount of powder and also capable of being reused when the powdered medicine storage chamber is replaced.

We claim:

1. A multi-dose powdered medicine administering device comprising: a device body (1); a storage chamber (3) detachably provided in the device body, the storage chamber (3) being capable of storing powdered medicine, the amount of which corresponds to a plurality of times of administering operations; an accommodation chamber (10) capable of accommodating powdered medicine, the amount of which corresponds to a single time of administering operation; a medicine dispensing means (6) movably attached to the device body for movement between a charging position and an administering position, the medicine dispensing means communicating the accommodation chamber with the storage chamber at said charging position (3a), the medicine dispensing means communicating the accommodation chamber with the outside of the device body at said administering position (51) so that the powdered medicine in the accommodation chamber can be administered; movement means (20,21) separate from said body and engageable with said medicine dispensing means for moving the medicine dispensing means between the charging position and the administering position; and a pump (8) mounted on said device body for injecting air into the storage chamber through the accommodation means at the charging position so that the powdered medicine in the storage chamber can be stirred, wherein a predetermined quantity of powdered medicine that has been stirred is charged from the storage chamber to the accommodation chamber by the suction force of the pump means and/or gravity.

2. The multi-dose powdered medicine administering device according to claim 1, wherein a storage chamber mount portion is provided on said device body and wherein said storage chamber (3) is cylindrical, and one end of said storage chamber with respect to the axial direction has an opening for charging and is attached to said storage chamber mount portion (2) of the device body (10), and the other end of said storage chamber is closed by a filter (14) through which air can be circulated but powdered medicine cannot be circulated.

3. The multi-dose powdered medicine administering device according to claim 1, wherein said dispensing means is composed of a rotor (60) having a rotational axis rotatably attached to the device body (1), a plurality of through-holes are formed at regular intervals around said rotational axis (0) of the rotor, a filter (11) through which air can be circulated but powdered medicine cannot be circulated is inserted and fixed to each through-hole, said accommodation chamber (10) is defined by the filter, and pushing means (30, 31, 32) mounted of said device body for pushing said rotor into engagement with a portion (1a) of the device body whereby the opening of the accommodation chamber (10) can be closed by the portion (1a) of the device body while the accommodation chamber moves from a charging position (3a) to an administering position (5a).

4. The multi-dose powdered medicine administering device according to claim 3, wherein said device body (1) includes a flat plate portion (1a) at one end of said device body, a charging opening and administering opening are respectively formed at the charging (3a) position and administering position (5a) on the flat plate, and a storage chamber mount portion (2) for detachably mounting said storage chamber (3) corresponding to the charging opening is provided on one side of said flat plate portion (1a).

5. The multi-dose powdered medicine administering device according to claim 4, wherein said rotor (6) is rotatably provided so that a surface of said accommodation chamber (10) on the opening side can be contacted with the other surface of said flat plate portion (1a), the chamber (10) can be contacted with an opposite surface of said flat plate portion (1a), the mount portion (2) of said flat plate portion, and the accommodation chamber of the rotor is aligned and communicated with the administering opening at the administering position (5a) in the axial direction.

6. The multi-dose powdered medicine administering device according to claim 5, wherein at least two accommodation chambers (10) are provided around said rotational axis of the rotor (6) at regular intervals such that, when the first accommodation chamber is located at the charging position (3a), the second accommodation chamber is located at the administering position (5a), when said rotor (6) is rotated at intervals of 180°, each accommodation chamber (10) is alternately located at the charging and administering positions, and the accommodation chamber (10) is contacted with and closed by the flat plate portion (1a) when the accommodation chamber (10) is located between the charging and administering positions.

7. The multi-dose powdered medicine administering device according to claim 5, wherein four accommodation chambers are provided around said rotational axis of the rotor (6) at intervals of 90°, the charging opening at the charging position (3a) and the administering opening at the administering position (5a) are symmetrically located with respect to the axis at intervals of 180° in said flat plate portion (1a), said rotor (6) is rotated at intervals of 90°, and the four accommodation chambers (10) are successively located at the charging position, administration waiting position, administering position, and charge waiting position.

8. The multi-dose powdered medicine administering device according to claim 4, further comprising draft means mounted on said device body wherein said rotor (6) is sandwiched between said flat plate portion (1a) and said draft means, (7) said pushing means including a pin (30) extending through said flat plate portion, said rotor and said draft means on said rotational axis and a spring (31) engaging with the pin and said draft means so that the rotor (6) is rotatably held by the pin (30), and said spring presses said draft means and flat plate portion into contact with opposite surfaces of said rotor.

9. The multi-dose powdered medicine administering device according to claim 8, wherein said draft means (7) includes air passages (3b, 5b) communicated with said accommodation chambers (10) through said filter (11) at said charging position (3a) and said administering position (5a).

10. The multi-dose powdered medicine administering device according to claim 9, wherein a two-way valve (71) is provided in an air passage communicated with the accommodation chamber (10) at said charging position (3a), and a one-way valve (71) through which air is allowed to flow only to the accommodation chamber side is provided in an air passage communicated with the accommodation chamber (10) at said administering position (5a).

11. The multi-dose powdered medicine administering device according to claim 3, wherein the device body (1)

includes a flat plate portion (1a) at one end of said body device, a charge opening and an administration opening are formed at the charging position (3a) and the administering position (5a) of the flat plate portion, a storage chamber mount portion (2) is provided on one surface of the flat plate (1a) so that the storage chamber (3) can be detachably mounted corresponding to the charge opening, and the pump means (8) is composed of a returnable and flexible container attached on an opposite end of the device body, and the pump means supplies and sucks air only from the accommodation chamber (10) located at the charging position (3a) through the filter (11) wherein the supplying and sucking operation is conducted from a side of the rotor (6) opposite to the flat plate portion (1a).

12. The multi-dose powdered medicine administering device according to claim 3, wherein the device body (1) includes a flat plate portion (1a) at one end of said body device, a charging opening and an administering opening formed at the charging position (3a) and the administering position (5a) of the flat plate portion, a storage chamber mount portion (2) provided on one surface of the flat plate (1a) for detachably mounting the storage chamber (3) on the charge opening, a nozzle mount portion (4), a nozzle (5) having an injection opening (5b) at one end thereof is attached to one surface of the flat plate (1a) adjacent to the administration opening, and said pump means (8) composed of a returnable and flexible container attached to the device body, and the pump means located at the charging position (3a) and the administering position (5a) through the filters (11) wherein the supplying and sucking operation is conducted from a side of the rotor (6) opposite to the flat plate portion (1a).

13. The multi-dose powdered medicine administering device according to claim 3, wherein the device body (1) is composed of a disk portion (1a) and a cylinder portion (1b) formed integrally with the outer circumference of the disk portion, the rotor (6) having an outer circumferential surface and opposite axially directed surfaces is rotatably held inside the cylinder portion (1b) so that one axially directed surface of the rotor is maintained in a contact condition with the disk portion (1a), a guide groove (12) is formed in the cylinder portion of the device body, a helical groove (13) is formed on the outer circumferential surface of the rotor (6), a cap (20) capable of being attached to and detached from the cylinder portion (1b), a cam pin (21) carried on an inner surface of said cap penetrating through said guide groove (12) and engaging with said helical groove (13), each time the cap (20) is attached to and detached from the cylinder portion, wherein said rotor (6) is rotated in a predetermined direction by a predetermined angle, when the cap is detached, to position the plurality of accommodation chambers (10) at the charging position (3a) and the administering position (5a), and when the cap is attached, every accommodation chamber (10) is positioned between the charging position (3a) and the administering position (5a) so that each accommodation chamber (10) is closed by the disk portion (1a) of the device body (1).

14. An inhalation type feed method for feeding multi-dose powdered medicine to be administered, comprising the steps of: attaching a storage chamber (3) for storing powdered medicine, the amount of which corresponds to a plurality of times of administering operations, to a device body (1); moving a quantitative medicine dispensing means (6) having an accommodation chamber (10), the capacity of which corresponds to a single administering operation, to a charging position at which said accommodation chamber is communicated with said storage chamber; stirring the powdered medicine in said storage chamber by injecting air into said storage chamber through said accommodation chamber at the charging position; charging the powdered medicine, the amount of which corresponds to a single administering operation, from said storage chamber into said accommodation chamber by the action of gravity and/or suction force; and moving said dispensing means (6) so that the accommodation chamber (10) charged with the powdered medicine can be conveyed to the administering position.

15. The inhalation type feed method according to claim 14, wherein said powdered medicine dispensing means (6) includes at least two accommodation chambers (10), and moving said dispensing means (6) for conveying the first accommodation chamber to the charging position and simultaneously conveying the second accommodation chamber to the administering position.

16. A spraying type feed method for feeding multi-dose powdered medicine to be administered, comprising the steps of: attaching a storage chamber (3) for storing powdered medicine, the amount of which corresponds to a plurality of times of administering operations, to a device body (1); moving a quantitative medicine dispensing means (6) having an accommodation chamber (10), the capacity of which corresponds to a single administering operation, to a charging position at which said accommodation chamber is communicated with said storage chamber; stirring the powdered medicine in said storage chamber by injecting air into said storage chamber through said accommodation chamber at the charging position; charging the powdered medicine, the amount of which corresponds to a single administering operation, from said storage chamber into said accommodation chamber by the action of gravity and/or suction force; moving said dispensing means (6) so that the accommodation chamber (10) charged with the powdered medicine can be conveyed to the administering position; and injecting air into said accommodation chamber at the administering position so that the powdered medicine, the amount of which corresponds to a single administering operation, is sprayed outside the device body.

17. The spraying type feed method according to claim 16, wherein said powdered medicine dispensing means (6) includes at least two accommodation chambers (1), and moving said dispensing means (6) for conveying the first accommodation chamber to the charging position and simultaneously conveying the second accommodation chamber to the administering position, and said air injecting operation at the administering position are simultaneously carried out by the same pump means (8).

18. A quantitative feed device for quantitatively feeding powder comprising: a device body (1); a storage chamber (3) detachably provided to said device body, the capacity of which corresponds to a plurality of times of feeding operations; an accommodation chamber (10), the capacity of which corresponds to a single time of feeding operation; a quantitative dispensing means (6) movably attached to said device body for movement to a charging portion and a feeding position so that the powdered medicine can be supplied to the accommodation chamber when the accommodation chamber is communicated with the storage chamber at the charging position (3a) and the accommodation chamber is communicated outwardly of the device body (1) at the feeding position (5a); means (20, 21) for moving said dispensing means between the charging and feeding positions; and a pump means (8) for stirring the powder in the storage chamber by injecting air into said storage chamber through said accommodation chamber, wherein a predetermined amount of stirred powder is charged from said storage chamber to said accommodation chamber by the action of suction force generated by said pump means and/or the action of gravity.

* * * * *